United States Patent [19]

Crapps

[11] Patent Number: 5,185,447
[45] Date of Patent: Feb. 9, 1993

[54] POLYCYCLIC KETONES AND PREPARATIVE METHODS THEREFOR

[75] Inventor: Edward C. Crapps, New Castle, Del.

[73] Assignee: Du Pont Merck Pharmaceutical Company, Wilmington, Del.

[21] Appl. No.: 827,429

[22] Filed: Jan. 29, 1992

[51] Int. Cl.⁵ .................. C07D 487/04; C07D 221/16; C07C 45/54; C07C 49/447
[52] U.S. Cl. ..................................... 546/86; 546/111; 568/309; 568/326
[58] Field of Search ................... 546/86, 111; 568/309

[56]  References Cited

U.S. PATENT DOCUMENTS 3,723,535  3/1973  Brennon .............................. 568/383
4,873,250 10/1989  Hufford et al. ..................... 514/290

OTHER PUBLICATIONS

Dickeson et al., Aust. J. Chem. 1970, 23:1023.
Inglett and Smith, J. Am. Chem. Soc. 1950, 72:842.
Smith et al., J. Org. Chem. 1947, 12:781.
Kloc et al., Journal f. Prakt. Chemie, 1977, 319 (6):959.
Eckhard et al., Aust. J. Chem. 1973, 26:2727.

*Primary Examiner*—C. Warren Ivy
*Assistant Examiner*—Barbara Twardzik
*Attorney, Agent, or Firm*—Blair Q. Ferguson; Joe Lucci

[57]  ABSTRACT

Ketones having formulas (1)-(3) are provided by improved methods which involve the treatment of compounds having formulas (9)-(11) with aqueous base.

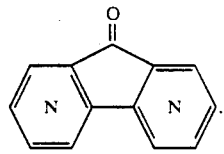

(1)

-continued

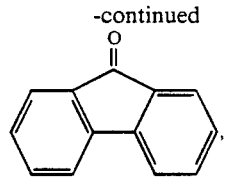
(2)

or

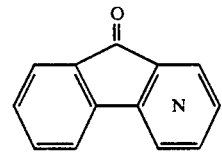
(3)

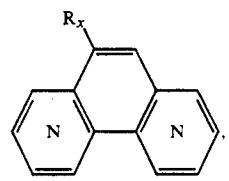

(9)

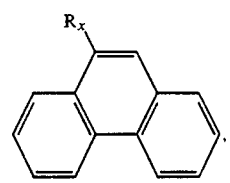

(10)

or

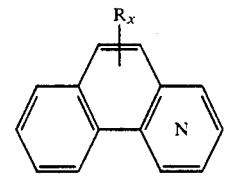
(11)

wherein $R_x$ is $NO_2$.

16 Claims, No Drawings

POLYCYCLIC KETONES AND PREPARATIVE METHODS THEREFOR

FIELD OF THE INVENTION

This invention relates to the synthesis of polycyclic ketones useful in the preparation of agents for the treatment of cognitive or neurological dysfunction in mammals and, more particularly, to the development of improved methods for preparing these polycyclic ketones.

BACKGROUND OF THE INVENTION

Certain polycyclic gem substituted ketones having mixed pendant groups have been found to enhance the stimulus-induced release of neurotransmitters in brain tissues and, thus, to improve processes involving learning memorization of active avoidance tasks. Compounds of interest have the formula:

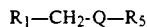

wherein:

Q is

Q is

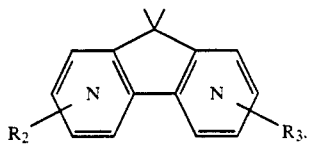

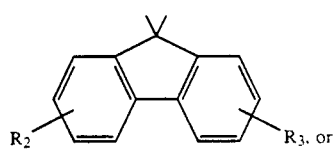

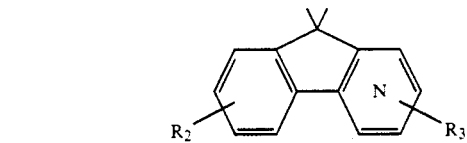

$R_1$ is a heterocyclic aromatic moiety such as a 4-, 3-, or 2-pyridyl, pyrimidyl, pyrazinyl, or fluoro-4-pyridyl group;

$R_2$ and $R_3$ are independently H, F, Cl, Br, $NO_2$, OH, $R_4$, $OR_4$, $CO_2R_4$, $COR_4$, $CONH_2$, $CONHR_4$, $CON(R_4)(R_4')$, $S(O)_m$—$R_4$, $NH_2$, $CF_3$, $NHR_4$, or $N(R_4)(R_4')$;

$R_4$ and $R_4'$ are independently H, alkyl having from about 1 to about 4 carbon atoms, $CH_2$Phe-W, or Phe-W;

Phe is a phenyl group;

$R_5$ is —$(CH_2)_n$—Y or —$OCOR_4$;

Y is H, OH, $NH_2$, $NHR_4$, $N(R_4)(R_4')$, $NHCOR_4$, $NHCO_2R_4$, $NHS(O)_2R_4$, F, Cl, Br, $OR_4$, $S(O)_mR_4$, $CO_2H$, $CO_2R_4$, CN, $CON(R_4)(R_4')$, $CONHR_4$, $CONH_2$, $COR_4$, Phe, Phe-W, —C≡$CCO_2R_4$, —CH=$CHR_4$, —C≡$CR_4$, or a heterocyclic aromatic moiety such as a 4-, 3-, or 2-pyridyl, pyrimidyl, pyrazinyl, or fluoro-4-pyridyl group;

W is F, Cl, Br, $R_4$, OR, $NO_2$, $NH_2$, $NHR_4$, $N(R_4)(R_4')$, CN, or $S(O)_m$—$R_4$;

m is 0, 1, or 2; and n is about 1-7.

A number of proposed syntheses for these compounds employ polycyclic ketones having formulas (1)-(3) as starting materials.

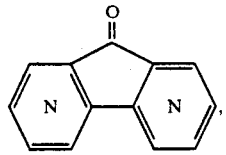

(1)

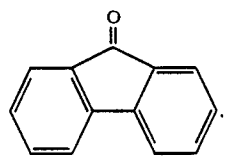

(2)

or

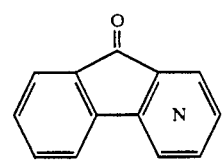

(3)

Certain of the polycyclic ketones are commercially available. For example, 4,5-diazafluoren-9-one can be obtained from GFS Chemicals (Columbus, Ohio). To date, however, it generally has not been possible to synthesize ketones of this type except through low-yielding procedures. For example, Dickeson, et al., *Aust. J. Chem.*, 1970, 23, 1023, disclosed a four-step synthesis of 4,5-diazafluoren-9-one (8) from phenanthroline (4) in 15% overall yield. The synthesis involved the reduction of 5-nitro-1,10-phenanthroline (5) to 5-amino-1,10-phenanthroline (6), which was oxidized to 1,10-phenanthroline-5,6-quinone (7). Quinone (7) was treated with aqueous alkali to give the ketone (8).

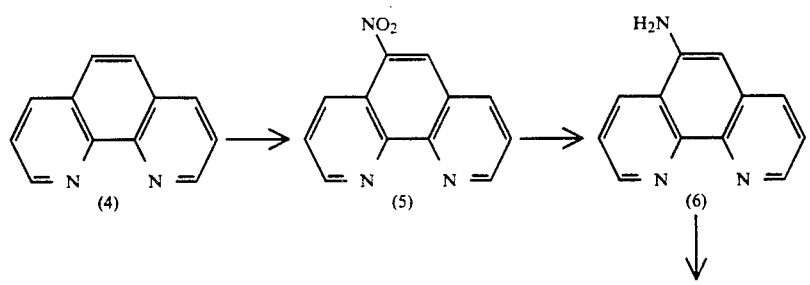

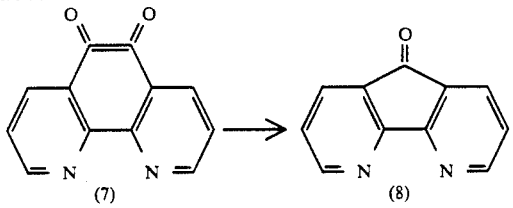

Inglett and Smith, *J. Am. Chem. Soc.*, 1950, 72, 842 disclosed synthesizing 4,5-diazafluoren-9-one (8) in less than 10% overall yield by treating the nitration filtrate of phenanthroline (4) with aqueous sodium hydroxide solution. Earlier, Smith, et al., *J. Org. Chem.*, 1947, 12, 781, had reported that the nitration filtrate contains 1,10-phenanthroline-5,6-quinone (7).

Kloc, et al., *Journal f. Prakt. Chemie.*, 1977, Band 319, Heft 6, 959, reported a one-step synthesis of 4,5-diazafluoren-9-one (8) in about 55% yield by oxidizing 1,10-phenanthroline (4) in alkaline permanganate. However, Echard, et al., *Aust. J. Chem.*, 1973, 26, 2727, reported 2,2'-dipyrido-3,3'-dicarboxylic acid as the major product of this reaction.

Accordingly, there exists a need in the art for more efficient and effective methods for synthesizing polycyclic ketones such as those having formulas (1)-(3).

SUMMARY OF THE INVENTION:

The present invention provides processes for preparing ketones having formulas (1)-(3):

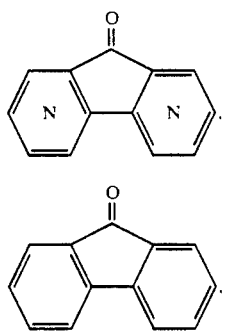

(1)

(2)

or

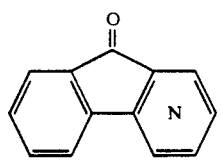

(3)

In general, these processes comprise providing a first compound having formula (9)-(11):

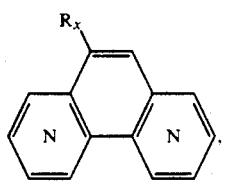

(9)

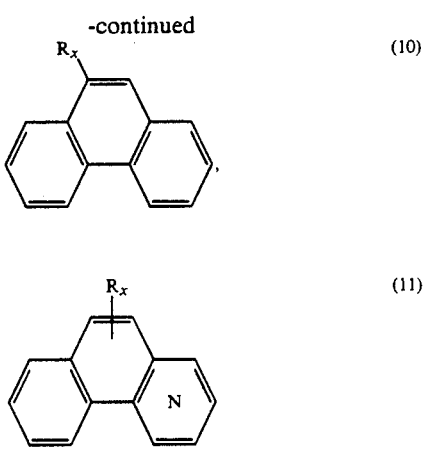

(10)

or (11)

wherein $R_x$ is an electron withdrawing group such as $NO_2$ or $SO_2R_6$ and $R_6$ is alkyl or aryl having from 1 to about 7 carbon atoms, and then mixing the first compound with aqueous base for a time and under reaction conditions effective to form said ketone.

In general, the novel synthetic processes of the present invention are considerably more simple and straightforward than those of the prior art and provide compounds having formulas (1)-(3) in significantly higher yield.

DETAILED DESCRIPTION OF THE INVENTION

The polycyclic ketones of the present invention are generally synthesized by treating one or more substituted phenanthrolines, phenanthrenes, or azaphenanthrenes having formula (9)-(11) with aqueous base. One preferred such compound is 5-nitro-1,10-phenanthroline (5). Substituted compounds having formula (9)-(11) can be synthesized by any of the means known in the art, preferably by nitration of the corresponding phenanthroline, phenanthrene, or azaphenanthrene by the procedures disclosed by Inglett, et al., *J. Am. chem. Soc.*, 1950, 72, 842 and by Smith, et al., *J. Org. Chem.*, 1947, 12, 781.

According to the present invention, substituted compounds having formula (9)-(11) are treated with base, preferably aqueous base, for a time and under reaction conditions effective to form ketones having formula (1)-(3). Representative bases include metal hydroxides, metal alkoxides having from about 1 to about 7 carbon atoms, metal hypohalites, and combinations thereof. Preferred bases comprise alkali metal hydroxide; sodium hydroxide is particularly preferred. The base may be provided in any of the forms known in the art at wide variety of concentrations, so long as the reaction system is carefully monitored to avoid undue hydrolysis of compounds (9)-(11). In general, more concentrated bases will require shorter reaction times but will present the risk of producing unwanted by-products. Optimally, the compounds of formula (9)–(11) are treated with base in the presence of a metal carboxylate having from about 1 to about 7 carbon atoms. Alkali metal carboxylates are preferred; potassium oxalate is particularly preferred. In preferred embodiments, from about 0.04 to about 0.95 equivalents (preferably about 0.78 equivalents) alkali metal hydroxide are added along with from about 1.1 to about 3.2 equivalents (preferably 1.6 equivalents) alkali metal carboxylate at a temperature from about 80° C. to about 123° C. (preferably about 94°–100° C.)

Care should be taken to monitor reaction completion in embodiments wherein compounds having formula (9)–(11) are treated with base in the absence of metal carboxylate. Unduly short and unduly long reaction times are to be avoided. Short reaction times will result in an incomplete conversion of starting material, while products (1)–(3) appear to decompose upon prolonged exposure to base. In general, it is preferred that reactions involving the treatment of compounds having formula (9)–(11) with base be monitored by high performance liquid chromatography (HPLC) or gas chromatography (GC) rather than by thin layer chromatography (TLC) and that the resulting product be isolated promptly upon substantial completion of the reaction.

Additional objects, advantages, and novel features of this invention will become apparent to those skilled in the art upon examination of the following examples thereof, which are not intended to be limiting. Parts and percents are by weight unless otherwise noted.

EXAMPLE 1

Preparation of 5-Nitro-1,10-phenanthroline (Formula (5))

Fuming sulfuric acid (667 ml, 104%) was placed in a 3.0 liter, three-neck, round bottom flask equipped with an air stirrer, a thermocouple, a gas venting powder funnel with a nitrogen inlet, and a condenser connected to a scrubber.

Dry 1,10-phenanthroline (formula (4), 400 g, 2.22 moles) was placed into the powder funnel under nitrogen atmosphere. The phenanthroline was then added to the sulfuric acid. The rate of addition was selected to maintain a pot temperature less than 100° C. through occasional immersion in an ice water bath. The addition of the phenanthroline took about 1.0–1.5 hours.

The powder funnel then was replaced by a gas venting addition funnel, which was subsequently filled with 534 ml of 90% fuming nitric acid. The pot temperature was kept below 115° C. by immersion in an ice water bath and by adjusting the rate of addition of the nitric acid. Once the addition was complete, the ice bath was replaced with a heating mantle and the reaction temperature maintained between 104°–115° C. The progress of the reaction was monitored by TLC for the disappearance of 1,10-phenanthrene ($R_f=0.14$) and the appearance of 5-nitro-1,10-phenanthrene ($R_f=0.51$) on silica gel using as the eluent 2% water/30% methanol/25% acetone/43% chloroform to which 4 drops concentrated ammonium hydroxide had been added. The reaction generally was complete in about 3.0–3.5 hours after addition of the nitric acid.

Once complete, the reaction solution was poured onto about 4 kg of ice with minimum stirring, forming the acid salt of 5-nitro-1,10-phenanthrene as a tan solid. This mixture was brought to pH 7 by addition of 50% sodium hydroxide, maintaining a temperature less than or equal to 35° C. The tan product was filtered through a Dacron ®filter and washed with copious amounts of water. After drying, 516 grams of an 84% pure crude product was obtained. A portion of the crude product recrystallized from methanol/water had a melting point of 199.1°–201.1° C.

EXAMPLE 2

Preparation of 4,5-Diazafluoren-9-one (Formula (8)) 2a. Trial 1

5-Nitro-1,10-phenanthroline (formula (5), 100.2 grams; 0.44 moles), potassium oxalate (378.7 grams; 2.05 moles), water (1500 mL), and 12.5% aqueous sodium hydroxide solution (500 mL) were added in that order to a three-neck, round bottom flask equipped with a reflux condenser, mechanical stirrer, thermocouple, and a nitrogen inlet and exit. This mixture was heated under nitrogen and refluxed at 100° C. The reaction's progress was followed by TLC on silica gel, eluting with 2% water/30% methanol/25% acetone/43% chloroform to which 4 drops concentrated ammonium hydroxide had been added. The reaction was complete in about 3–4 hours as judged by TLC. $R_f=0.64$ (5-nitro-1,10-phenanthroline) and 0.76 (4,5-diazafluoren-9-one).

The reaction mixture was cooled to room temperature using baths of luke warm water and then ice water. Ethyl acetate (1 liter) then was added to the stirred reaction mixture. The reaction mixture was filtered and the filter cake washed with 500 mL of ethyl acetate. The ethyl acetate layer was separated and the aqueous filtrate back extracted two times each with 1 liter ethyl acetate. The extracts were contained and washed with saturated aqueous sodium chloride solution, separated, dried over magnesium sulfate, filtered, and concentrated in vacuo. The crude product weighed 59.2 grams. The filter cake was slurried with 800 mL of chloroform. The slurry was washed with saturated sodium chloride solution, separated, dried over magnesium sulfate, filtered, concentrated in vacuo, chromatographed on 50 grams silica gel using chloroform as eluent, and recrystallized from ethanol/water to yield 10.5 grams pure ketone. The products were combined to give 69.7 grams ketone (86% yield from 5-nitro-1,10-phenanthroline, (5)). The sample is the same as authentic compound by TLC. IR(KBr): 1715cm$^{-1}$(s); $^1$H NMR(CDCl$_3$): 8.72 (dd, 3H and 6H, J=4.5 Hz and 2 Hz); 7.92 (dd, 1 Hz and 8 Hz, and 2 Hz); 7.30 (dd, 3H and 7H, J=4.5 Hz and 2 Hz). Analysis calculated for C$_{11}$H$_6$N$_2$O: C, 72.52; H, 3.32; N, 15.38. Found: C, 72.41; H, 3.14; N, 15.37. M.P.: 214.1°–216.1° C.

2b. Trial 2

5-Nitro-1,10-phenanthroline (10.4 grams; 0.0462 moles), potassium oxalate (44.0 grams; 0.24 moles), water (500 mL), and 12.5% aqueous sodium hydroxide solution (50 mL) were added in that order to a three-neck, round bottom flask equipped with a reflux condenser, mechanical stirrer, thermocouple, and a nitrogen inlet and exit. This mixture was heated under nitrogen and refluxed at about 95°–100° C. The reaction's progress was followed by TLC on silica gel, eluting with 2% water/30% methanol/25% acetone/43% chloroform to which 4 drops concentrated ammonium hydroxide had been added. The reaction was complete in 3 hours as judged by TLC.

The reaction mixture was cooled to room temperature using baths of luke warm water and then ice water, and extracted twice with 500 mL portions of chloroform. The extracts were combined and washed with saturated aqueous sodium chloride solution, separated, dried over magnesium sulfate, filtered, and concentrated in vacuo. The crude product (7 grams) was chromatographed on silica gel and recrystallized from ethanol/water to yield 6.61 grams pure ketone (79% yield from 5-nitro-1,10-phenanthroline, (5)).

2c. Trial 3

5-Nitro-1,10-phenanthroline (10.03 grams; 0.045moles), sodium acrylate (19.31 grams; 0.205 moles), water (100 mL), and 12.5% aqueous sodium hydroxide solution (50 mL) were added in that order to a three-neck, round bottom flask equipped with a reflux condenser, a mechanical stirrer, thermocouple, and a nitrogen inlet and exit. This mixture was heated under nitrogen and refluxed at about 100° C. The reaction's progress was followed by TLC on silica gel, eluting with 2% water/30% methanol/25% acetone/43% chloroform to which 4 drops concentrated ammonium hydroxide had been added. The reaction was complete in 7 hours as judged by TLC. The reaction solution was brown in color.

The reaction mixture was cooled to room temperature using baths of luke warm water and then ice water, and extracted with ethyl acetate. The extract was washed with saturated aqueous sodium chloride solution, separated, dried over magnesium sulfate, filtered, and concentrated in vacuo. The crude product was recrystallized from ethanol/water to yield 4 40 grams pure ketone (54% yield from 5-nitro-1,10-phenanthroline, (5)).

The reactions of Example 2 can be monitored by HPLC and by GC according to the following conditions:

HPLC Conditions

Instrument: HP 1090 HPLC
Column: Waters Nova-Pak phenyl (15 cm × 3.9 mm)
Oven: 40° C.
Detector: 243 nm
Injection vol: 10μl
Flow: 1.0 mL/min
Mobile Phase:
A) 5mM hexane sulfonate; 50 mM sodium phosphate monobasic monohydrate; 0.1% TEA; adusted to pH 2.5 with phosphoric acid
B) methanol

| Mobile Phase Prep: | |
| --- | --- |
| HPLC water | 1 L |
| 50 mM sodium phosphate monobasic monohydrate | 6.90 g |
| 5 mM hexane sulfonate | 941.1 g |
| 0.1% TEA | 1 mL |
| All chemicals were added together and then pH was adjusted to 2.5 with phosphoric acid. | |

| Gradient: | Time | % B |
| --- | --- | --- |
| | 0 | 30 |
| | 1 | 30 |
| | 26 | 65 |
| | 30 | 65 |
| | 33 | 30 |
| | 35 | 30 |

| Retention Time (min) | Compound |
| --- | --- |
| 11.2 | 5-nitro-1,10-phenanthroline |
| 7.5 | 4,5-diazafluoren-9-one |
| 6.1 | unknown intermediate that is converted to product in about 12 hours |

GC Conditions

GC samples are prepared by dissolving approximately 10 mg of the sample in methanol in a 10 mL volumetric flask. Sonication may be required. This solution can be serially diluted to establish a linear detector response range for the instrument.

Instrument: HP 5890 GC with capillary split/splitless injection or equivalent
Column: DB-1 (30 m × 0.53 mm)
Film Thickness: 5 μm
Carrier: He; 20.8 mL/min column, 33.2 mL/min column+aux., 297 mL/min split vent
Oven: 150° C. (1 min hold) to 260° C. (20° C./min), 15 min final time
Detector: FID 300° C.
Injector: 250° C.
Injector volume: 1μl

| Retention Time (min) | Compound |
| --- | --- |
| 11.7 | 5-nitro-1,10-phenanthroline |
| 6.7 | 4,5-diazafluoren-9-one |
| 8.2 | 1,10-phenanthroline |

This GC method can be used to detect 4,5-diazafluoren-9-one over a concentration range of from 1 to 1000 ppm. Sample carryover may be observed at concentrations greater than 1000 ppm. Carryover can be minimized by injecting methanol between sample injections. 1,10-phenanthroline and 5-nitro-1,10-phenanthroline can also be resolved using this method. Also, it will be noted that the above-described GC method employs a megabore (0.53mm ID) column. Use of a packed column such as an OV-1 or SE-30 column may yield acceptable results. However, further method development may be required when a packed column is used.

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. A process for preparing a ketone having one of the formulas:

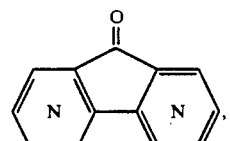

(1)

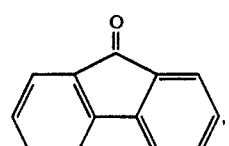

(2)

or

-continued

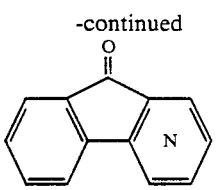
(3)

comprising the steps of:
providing a first compound having one of the formulas:

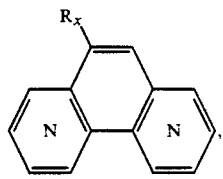
(9)

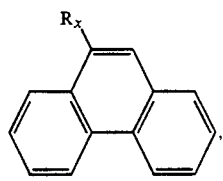
(10)

or

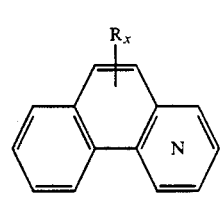
(11)

wherein $R_x$ is $NO_2$; and
contacting said first compound with aqueous base for a time and under reaction conditions effective to form said ketone.

2. The process of claim 1 wherein said base comprises metal hydroxide, metal alkoxide, metal hypohalite, or combinations thereof.

3. The process of claim 1 wherein said base comprises sodium hydroxide.

4. The process of claim 1 wherein said contacting is performed in the presence of metal carboxylate having from about 1 to about 7 carbon atoms.

5. The process of claim 1 wherein said contacting is performed in the presence of potassium oxalate.

6. A process for preparing 4,5-diazafluoren-9-one, comprising contacting 5-nitro-1,10-phenanthroline with aqueous base for a time and under reaction conditions effective to form said 4,5-diazafluoren-9-one.

7. The process of claim 6 wherein said base comprises metal hydroxide, metal alkoxide, metal hypohalite, or combinations thereof.

8. The process of claim 6 wherein said base comprises sodium hydroxide.

9. The process of claim 6 wherein said contacting is performed in the presence of metal carboxylate having from about 1 to about 7 carbon atoms.

10. The process of claim 6 wherein said contacting is performed in the presence of potassium oxalate.

11. A process for preparing a ketone having one of the formulas:

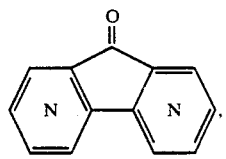
(1)

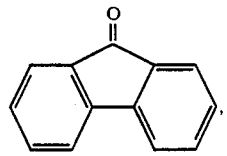
(2)

or

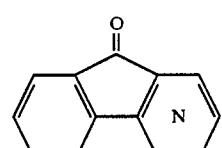
(3)

comprising the steps of:
providing a first compound having one of the formulas:

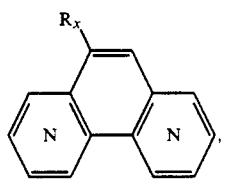
(9)

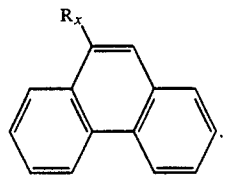
(10)

or

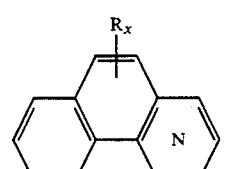
(11)

wherein $R_x$ is $NO_2$; and
reacting said first compound with aqueous base under conditions effective to form said ketone;
monitoring said reaction for said ketone; and
isolating said ketone from said mixture upon substantial completion of said reaction.

12. The process of claim 11 wherein said monitoring is performed using high performance liquid chromatography.

13. The process of claim 11 wherein said base comprises metal hydroxide, metal alkoxide, metal hypohalite, or combinations thereof.

14. The process of claim 11 wherein said base comprises sodium hydroxide.

15. The process of claim 11 wherein said first compound is 5-nitro-1,10-phenanthroline and said ketone is 4,5-diazafluoren-9-one.

16. A process for preparing 4,5-diazafluoren-9-one, comprising mixing 5-nitro-1,10-phenanthroline with sodium hydroxide and potassium oxalate for a time and under reaction conditions effective to form said 4,5-diazafluoren-9-one.

* * * * *